US010646159B2

(12) United States Patent
Kelly et al.

(10) Patent No.: US 10,646,159 B2
(45) Date of Patent: *May 12, 2020

(54) VISCERAL FAT MEASUREMENT

(71) Applicant: Hologic, Inc., Bedford, MA (US)

(72) Inventors: Thomas L. Kelly, Groveland, MA (US); Kevin E. Wilson, Acton, MA (US)

(73) Assignee: HOLOGIC, INC., Marlborough, MA (US)

( * ) Notice: Subject to any disclaimer, the term of this patent is extended or adjusted under 35 U.S.C. 154(b) by 742 days.

This patent is subject to a terminal disclaimer.

(21) Appl. No.: 14/788,864

(22) Filed: Jul. 1, 2015

(65) Prior Publication Data

US 2015/0374291 A1     Dec. 31, 2015

Related U.S. Application Data

(63) Continuation of application No. 13/045,966, filed on Mar. 11, 2011, now Pat. No. 9,086,356, which is a (Continued)

(51) Int. Cl.
*A61B 5/00*       (2006.01)
*A61B 6/00*       (2006.01)
(Continued)

(52) U.S. Cl.
CPC ............ *A61B 5/4872* (2013.01); *A61B 6/461* (2013.01); *A61B 6/482* (2013.01); *A61B 6/50* (2013.01);
(Continued)

(58) Field of Classification Search
CPC ....... A61B 5/4872; A61B 6/032; A61B 6/461; A61B 6/482; A61B 6/5217; A61B 6/5294;
(Continued)

(56) References Cited

U.S. PATENT DOCUMENTS 6,198,797 B1 *   3/2001   Majima ................. A61B 6/032
                                                       378/4
6,215,846 B1     4/2001   Mazess et al.
(Continued)

OTHER PUBLICATIONS

Kamel, Measurement of Abdominal Fat in Obese Men and Women, Obesity Research vol. 8 No. 1 Jan. 2000.*
(Continued)

*Primary Examiner* — Mark D Remaly
(74) *Attorney, Agent, or Firm* — Kriegsman & Kriegsman

(57) ABSTRACT

Dual-energy absorptiometry is used to estimate visceral fat metrics and display results, preferably as related to normative data. The process involves deriving x-ray measurements for respective pixel positions related to a two-dimensional projection image of a body slice containing visceral fat and subcutaneous fat, at least some of the measurements being dual-energy x-ray measurements, processing the measurements to derive estimates of metrics related to the visceral fat in the slice, and using the resulting estimates. Processing the measurements includes an algorithm which places boundaries of regions, e.g., a large "abdominal" region and a smaller "abdominal cavity" region. Two boundaries of the "abdominal cavity" region are placed at positions associated with the left and right innermost extent of the abdominal muscle wall by identifying inflection of % Fat values. The regions are combined in an equation that is highly correlated with VAT measured by quantitative computed tomography in order to estimate VAT.

12 Claims, 7 Drawing Sheets

Related U.S. Application Data continuation-in-part of application No. 12/730,051, filed on Mar. 23, 2010, now Pat. No. 9,179,873, which is a continuation of application No. 10/958,107, filed on Oct. 4, 2004, now Pat. No. 7,725,153.

(51) Int. Cl.
| | |
|---|---|
| *G06T 7/00* | (2017.01) |
| *G06T 7/11* | (2017.01) |
| *G01N 23/046* | (2018.01) |
| *G06K 9/46* | (2006.01) |
| *A61B 6/03* | (2006.01) |

(52) U.S. Cl.
CPC .......... *A61B 6/5217* (2013.01); *A61B 6/5294* (2013.01); *G01N 23/046* (2013.01); *G06K 9/46* (2013.01); *G06T 7/0012* (2013.01); *G06T 7/11* (2017.01); *A61B 6/032* (2013.01); *G01N 2223/419* (2013.01); *G01N 2223/612* (2013.01); *G06K 2009/4666* (2013.01); *G06T 2207/10116* (2013.01)

(58) Field of Classification Search
CPC ............... A61B 6/50; G01N 2223/419; G01N 2223/612; G01N 23/046; G06K 2009/4666; G06K 9/46; G06T 2207/10116; G06T 7/0012; G06T 7/11
See application file for complete search history.

(56) References Cited

U.S. PATENT DOCUMENTS

| | | | |
|---|---|---|---|
| 6,233,473 | B1 | 5/2001 | Shepherd et al. |
| 6,315,447 | B1 | 11/2001 | Nord et al. |
| 6,468,209 | B1 | 10/2002 | Heymsfield et al. |
| 6,816,564 | B2 | 11/2004 | Charles, Jr. et al. |
| 6,969,350 | B1 | 11/2005 | Hawthorne et al. |
| 6,999,549 | B2 | 2/2006 | Sabol et al. |
| 7,444,961 | B1 | 11/2008 | Ellis |
| 7,595,043 | B2 | 9/2009 | Hedrick et al. |
| 7,725,153 | B2 | 5/2010 | Kelly et al. |
| 8,300,911 | B1 | 10/2012 | Payne et al. |
| 8,792,689 | B2 | 7/2014 | Kelly et al. |
| 9,086,356 | B2 | 7/2015 | Kelly et al. |
| 9,179,873 | B2 | 11/2015 | Kelly et al. |
| 9,865,050 | B2 | 1/2018 | Kelly et al. |
| 2001/0053202 | A1 | 12/2001 | Mazess et al. |
| 2004/0077088 | A1* | 4/2004 | Charles, Jr. ............ A61B 6/032 435/455 |
| 2004/0101086 | A1 | 5/2004 | Sabol et al. |
| 2006/0074288 | A1 | 4/2006 | Kelly et al. |
| 2007/0223795 | A1* | 9/2007 | Qing ..................... G06T 7/155 382/128 |
| 2010/0086185 | A1 | 4/2010 | Weiss |
| 2010/0168551 | A1* | 7/2010 | Moller .................. A61B 5/0059 600/407 |
| 2010/0234719 | A1 | 9/2010 | Kelly et al. |
| 2011/0002522 | A1 | 1/2011 | Goto et al. |
| 2011/0158386 | A1 | 6/2011 | Payne et al. |
| 2011/0164798 | A1 | 7/2011 | Masumoto |
| 2011/0235886 | A1 | 9/2011 | Kelly et al. |
| 2011/0311122 | A1 | 12/2011 | Kelly et al. |
| 2015/0036910 | A1 | 2/2015 | Kelly et al. |
| 2016/0228057 | A1 | 8/2016 | Kelly et al. |
| 2018/0189948 | A1 | 7/2018 | Kelly et al. |

OTHER PUBLICATIONS

S.A. Gronenmeyer et al., "Fast Adipose Tissue (FAT) Assessment by MRI," Magnetic Resonance Imaging, 18 (2000) 815-818.

T. Hayashi et al., "Visceral Adiposity and the Prevalence of Hypertension in Japanese Americans," Circulation (2003) 108:1718-1723.

Hologic Clarity of Vision, Discovery QDR Series Advanced Point-of-Care Bone Health Assessment, Hologic Osteoporosis Assessment, May 2004.

Hologic Clarity of Vision, Explorer Fan-Beam DXA for the Cost-Conscious Practice, Hologic Osteoporosis Assessment, Jan. 2004.

T.L. Kelly et al., "DXA Body Composition: Theory and Practice," Appl Radia. (1988); vol. 49, No. 5:6 pp. 511-513.

J. Kobayashi et al., "A Novel Method of Measuring Intra-Abdominal Fat Volume Using Helical Computed Tomography," International Journal of Obesity (2002) 26, 298-402.

M. Krotkiewski et al., "Impact of Obesity on Metabolism in Men and Women. Importance of Regional Adipose Tissue Distribution," J Clin Invest. (1983) The American Society for Clinical Investigation, Inc. Sep. 1983 vol. 72: 1150-1162.

H. Kvist, et al., "Total and visceral adipose-tissue volumes derived from measurements with computed tomography in adult men and women: predictive equations 1-3," Am J. Clin Nutr, 1988, 48:1351-61.

C.J. Ley, "Sex-and menopause-associated changes in body-fat distribution," Am J. Clin Nut, 1993, 55:950-4.

C.T. Montague et al., "Perspectives in Diabetes the Perils of Portliness Causes and Consequences of Visceral Adiposity," Diabetes (2000) 49:883-888.

Morricone L. et al., "Relationship of Visceral Fat Distribution to Angiographically Assessed Coronary Artery Disease: Results in Subjects With or Without Diabetes or Impaired Glucose Tolerance," PMID:12616807 [PubMed-indexed for MEDLINE], Nutr Metab Cardiovasc Dis. Oct. 2002 12(5):275-283.

B.J. Nicklas, et al., "Visceral Adipose Tissue Cutoffs Associated With Metabolic Risk Factors for Coronary Heart Disease in Women," Epidemiology/Health Services/Psychosocial Research, Diabetes Care May 2003 vol. 26: 1413-1420.

J.E. Pritchard et al., "Evaluation of Dual Energy X-Ray Absorptiometry as a Method of Measurement of Body Fat," European Journal of Clinical Nutrition (1993) 47, 216-228.

D.O. Slosman et al., "Assessment of Whole-Body Composition With Dual-Energy X-Ray Absorptiometry," Radiology (1992) 185:593-598.

M.S. Trueth et al., Estimating Intraabdominal Adipose Tissue in Women by Dual-Energy X-Ray Absorptiometry, Am J. Clin. Nutr (1995) vol. 62:427-432.

Hill et al., "Estimating Abdominal Adipose Tissue with DXA and Anthropometry," Obesity, 15(2):504-510 (Feb. 2007).

Jensen et al., "Measurement of abdominal and visceral fat with computed tomography and dual-energy x-ray absorptiometry," Am J Clin Nutr., 61(2):274-8 (Feb. 1995).

Bertrin et al., "Measurement of visceral adipose tissue by DXA combined with anthropometry in obese humans," Int J Obes Relat Metab Disord., 24(3):263-70 (Mar. 2000).

Kobayashi et al., "A novel method of measuring intra-abdominal fat volume using helical computed tomography," International Journal of Obesity, 26:398-402 (2002).

Bertin et al., "Measurement of visceral adipose tissue by DXA combined with anthropometry in obese humans," International Journal of Obesity, 24: 263-270 (2000).

\* cited by examiner

VISCERAL FAT MEASUREMENT

CROSS-REFERENCE TO RELATED APPLICATIONS

This application is a continuation of U.S. patent application Ser. No. 13/045,966, titled VISCERAL FAT MEASUREMENT, filed Mar. 11, 2011, which, in turn, is a continuation-in-part of U.S. patent application Ser. No. 12/730,051, titled ESTIMATING VISCERAL FAT BY DUAL-ENERGY X-RAY ABSORPTIOMETRY, filed Mar. 23, 2010, which, in turn, is a continuation of U.S. patent application Ser. No. 10/958,107, titled ESTIMATING VISCERAL FAT BY DUAL-ENERGY X-RAY ABSORPTIOMETRY, filed Oct. 4, 2004, now U.S. Pat. No. 7,725,153, all of which are incorporated herein by reference.

BACKGROUND OF THE INVENTION

Obesity can be generally predictive of morbidities such as coronary artery disease and diabetes, and the anatomical distribution of adipose tissue (fat) can be a strong independent predictor of these and other medical conditions and outcomes. For example, overweight subjects with a larger proportion of fat stored as visceral adipose tissue (VAT) are believed to be at a higher risk than similarly overweight individuals with a larger percentage of fat stored as subcutaneous adipose tissue (SAT). Studies have shown that VAT levels are a predictor of cardiovascular risk factors, e.g. HDL, LDL, triglyceride levels, and hypertension. Because of the predictive and other values of visceral fat as distinguished from general obesity and subcutaneous fat, it is believed desirable to find a way to efficiently and effectively measure or estimate VAT.

It is known in the art to measure or estimate VAT by differentiating it from SAT in abdominal cross-sections or slices using computerized tomography (CT) and magnetic resonance imaging (MRI). Measurements can be made at the level of the umbilicus, where SAT and VAT volumes typically are identified by an image thresholding algorithm. However, the relatively high cost of both examinations and the high radiation dosage of CT can discourage the use of these techniques as a screening tool for VAT levels. Further, the thresholding method lacks specificity because areas or volumes above the threshold can have different amounts of % fat, and areas or volumes below the threshold may not be fat-free. Thus, systematic errors can be introduced by assumptions of % fat in areas or volumes above or below the threshold.

Dual-energy x-ray absorptiometry (DXA) exams are widely available, rapid, relatively low dose, and much less costly than CT and MRI exams. Further, DXA is capable of measuring both global and regional fat mass because, for tissue paths that are projected as pixels in the x-ray image, a given dual-energy x-ray measurements pertains to a unique combination of fat and lean mass. However, the ability of DXA to distinguish between VAT and SAT has been limited because DXA is a two-dimensional projection technique.

SUMMARY OF THE INVENTION

In accordance with one non-limiting aspect of the invention a method comprises acquiring x-ray measurements for respective pixel positions related to a two-dimensional projection image of a portion of a subject's abdomen, wherein at least some of the measurements are dual-energy x-ray measurements; placing a plurality of regions of the image; computer processing to combine the plurality of regions to provide an estimate of visceral fat; and providing and displaying selected results related to said estimate of visceral fat.

In accordance with another non-limiting aspect of the invention a method comprises acquiring x-ray measurements for respective pixel positions related to a two-dimensional projection image of a portion of a subject's abdomen, wherein at least some of the measurements are dual-energy x-ray measurements; placing a first region of the image which extends from a first side of the abdomen to a second side of the abdomen; placing a second region which extends across an inner abdominal cavity wall from the first side to the second side between innermost extents of an abdominal muscle wall; computer processing the first and second regions to provide an estimate of visceral fat; and providing and displaying selected results related to said estimate of visceral fat.

In accordance with another non-limiting aspect of the invention a method comprises acquiring x-ray measurements using a dual-energy x-ray absorptiometry (DXA) system for respective pixel positions related to a two-dimensional projection image of a portion of a subject's abdomen, wherein at least some of the measurements are dual-energy x-ray measurements; placing a plurality of regions of the image in which the image is obtained using the DXA system, wherein said placing includes placing a first region of the image which extends from a first side of the abdomen to a second side of the abdomen, and placing a second region on or within the first region; computer processing to combine the plurality of regions to provide an estimate of visceral fat (VAT) in which said estimate of visceral fat is distinguishable from subcutaneous fat (SAT); and providing and displaying selected results related to said estimate of visceral fat in which said selected results of visceral fat is distinguishable from subcutaneous fat.

In accordance with another non-limiting aspect of the invention a method comprises acquiring x-ray measurements for respective pixel positions related to a two-dimensional projection image of a portion of a subject's abdomen, wherein at least some of the measurements are dual-energy x-ray measurements; placing a plurality of regions of the image; computer processing to combine the plurality of regions to provide an estimate of visceral fat, wherein combining the plurality of regions uses polynomial expansion; and providing and displaying selected results related to said estimate of visceral fat.

In accordance with another non-limiting aspect of the invention a method comprises acquiring x-ray measurements for respective pixel positions related to a two-dimensional projection image of a portion of a subject's abdomen, wherein at least some of the measurements are dual-energy x-ray measurements; placing a plurality of regions of the image, wherein the placing includes placing a first region of the image which extends from a first side of the abdomen to a second side of the abdomen and placing a second region which extends across an inner abdominal cavity from the first side to the second side between innermost extents of an abdominal muscle wall, and wherein said placing of said second region includes identifying a left and a right innermost extent of abdominal muscle wall by identifying inflection of adipose tissue values; computer processing to combine the plurality of regions to provide an estimate of visceral fat, wherein the computer processing includes computer processing at least some of the x-ray measurements for placing the second region of the image; and providing and displaying selected results related to said estimate of visceral fat.

In accordance with another non-limiting aspect of the invention a method comprises acquiring x-ray measurements for respective pixel positions related to a two-dimensional projection image of a portion of a subject's abdomen, wherein at least some of the measurements are dual-energy x-ray measurements; placing a plurality of regions of the image, wherein the placing includes placing a first region of the image which extends from a first side of the abdomen to a second side of the abdomen and placing a second region which extends across an inner abdominal cavity from the first side to the second side between innermost extents of an abdominal muscle wall; computer processing to combine the plurality of regions to provide an estimate of visceral fat, wherein the first region and the second region are combined in a linear equation that is correlated with visceral fat measured by quantitative computed tomography for processing the first and second regions to provide an estimate of visceral fat and wherein visceral fat is calculated as J*second region Mass−K*(first region Mass−second region Mass)+b; and providing and displaying selected results related to said estimate of visceral fat.

In accordance with another non-limiting aspect of the invention an apparatus comprises a data acquisition unit including a scanner that acquires x-ray measurements for respective pixel positions related to a two-dimensional projection image of a portion of a subject's abdomen, wherein at least some of the measurements are dual-energy x-ray measurements; a memory in which is placed a plurality of regions of the image; a processing unit that computer-processes the regions to provide an estimate of visceral fat; and a display unit that provides and displays selected results related to visceral fat of the subject.

In accordance with another non-limiting aspect of the invention an apparatus comprises a data acquisition unit including a scanner that acquires x-ray measurements for respective pixel positions related to a two-dimensional projection image of a portion of a subject's abdomen, wherein at least some of the measurements are dual-energy x-ray measurements; a memory in which is placed a first region of the image which extends from a first side of the abdomen to a second side of the abdomen, and a second region which extends across an inner abdominal cavity wall from the first side to the second side between innermost extents of an abdominal muscle wall; a processing unit that computer-processes the first and second regions to provide an estimate of visceral fat; and a display unit that provides and displays selected results related to visceral fat of the subject.

In various non-limiting alternatives one or more functions can be automated or partially automated with computer processing. For example, the first region can be automatically placed by a software tool using various anatomical landmarks and the position of an upper region of interest line delineating the pelvis for reference. Further, the software tool may automatically place the second region based on % Fat inflection which is indicative of the innermost extent of the abdominal muscle wall. Further, measurements of total adipose tissue in a fixed thickness region across the entire width of the subject, e.g., just above the pelvis at the level of the $4^{th}$ lumbar vertebrae, can be combined with a measurement of the adipose tissue in the same thickness region of the abdominal cavity plus whatever subcutaneous fat is present above and below the cavity region using a linear equation that is correlated with VAT measured by quantitative computed tomography in order to estimate VAT.

BRIEF DESCRIPTION OF THE FIGURES

FIG. 2b is an enlarged view of the portion of the image corresponding to the body slice indicated by a broken line rectangle in FIG. 2a.

DETAILED DESCRIPTION

Figure 1:
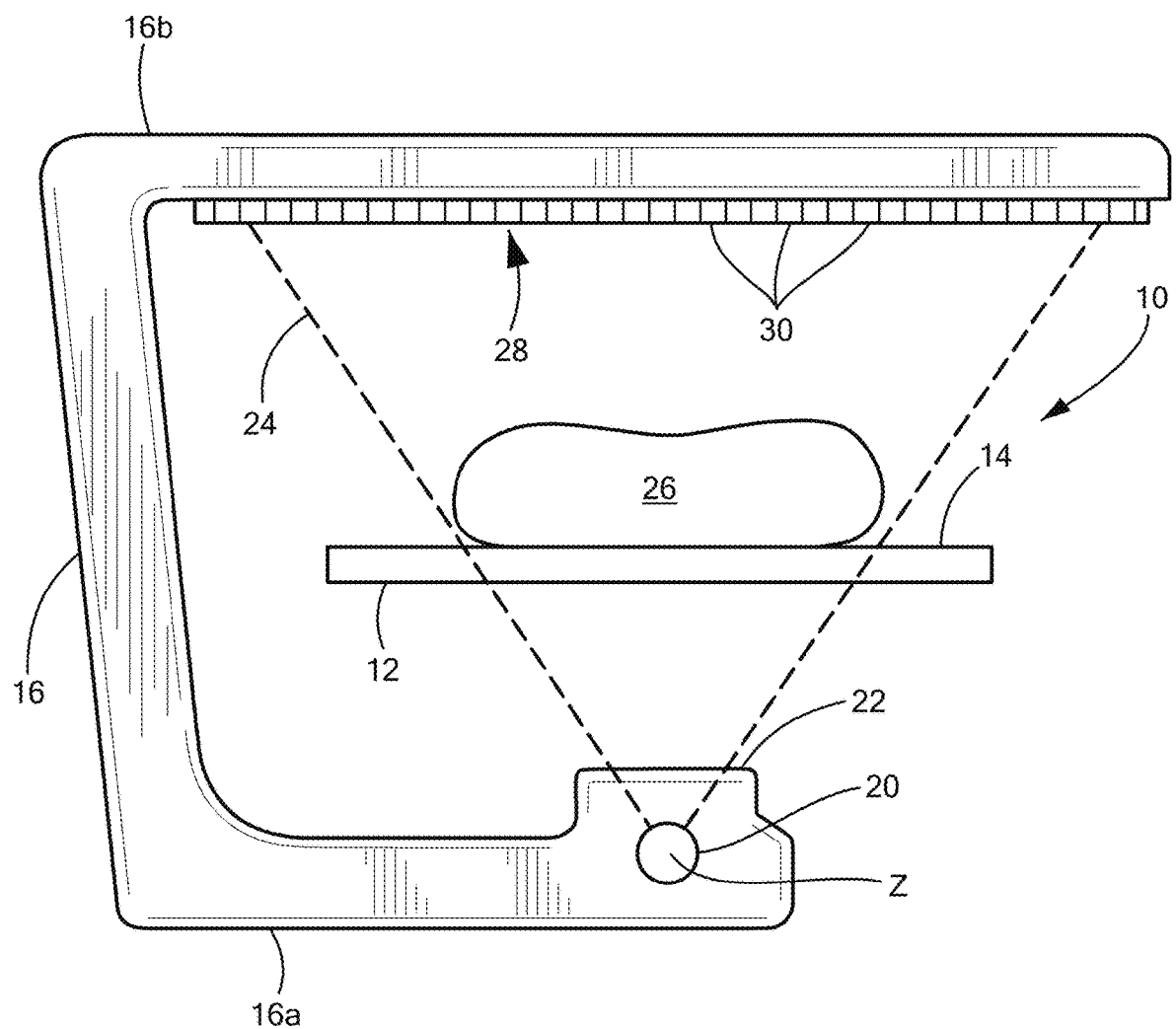
FIG. 1 is a simplified and schematic cross-sectional elevation illustrating a fan-shaped distribution of x-rays in a DXA system in which the visceral fat analysis described herein can be practiced.

Referring to FIG. 1, a DXA system 10 includes a patient table 12 having a support surface 14 that can be considered horizontal and planar in this simplified explanation and illustration which is not necessarily accurate in scale or geometry, and which is used here solely to illustrate and explain certain principles of operation. A human subject 26 is supine on surface 14. The length of the patient is along a horizontal longitudinal axis defined as the y-axis and the patient's arms are spaced from each other along the x-axis. A C-arm 16 has portions 16a and 16b extending below and above table 10, respectively, and is mounted in suitable structure (not shown expressly) for moving at least parallel to the y-axis along the length of patient 26. Lower portion 16a of the C-arm carries an x-ray source 20 that can emit x-rays limited by an aperture 22 into a fan-shaped distribution 24 conforming to a plane perpendicular to the y-axis. The energy range of the x-rays can be relatively wide, to allow for the known DXA dual-energy x-ray measurements, or can be filtered or generated in a narrower range to allow for single energy x-ray measurements. The x-ray distribution can be continuous within the angle thereof or can be made up, or considered to be made up, of individual narrower beams. The x-ray distribution 24 can encompass the entire width of the patient as illustrated, or it can have a narrower angle so the entire patient can be covered only by several passes along the y-axis and the x-ray measurements from the several passes can be combined as is known in the art to simulate the use of a wider fan beam, as typical in current commercial DXA systems. Alternatively, a single, pencil-like beam of x-rays can be used to scan selected regions of the patient's body, e.g. in a raster pattern. The x-rays impinge on x-ray detector 28, which can comprise one or more linear arrays of individual x-ray elements 30, each linear array extending in the x-direction, or a continuous detector where measurements for different positions along the detector can be defined in some manner known in the art, or can be another form of detector of x-rays. C-arm 16 can move at least along the y-axis, or can be maintained at any desired position along that axis. For any one position, or any one unit of incremental travel in the y-direction of arm 16, detector 28 can produce one or several lines of raw x-ray data. Each line can correspond to a row of pixels in a resulting image, which row extends in a direction corresponding to the x-direction. Each line corresponds to a particular position, or range of positions, of the C-arm in its movement along the y-axis and/or a particular linear detector, and comprises a number of individual measurements, each for a respective detector element position in the line, i.e., represents attenuation that the x-rays have suffered in traveling from source 20 to a respective detector element position over a specified time interval. A DXA system takes a higher x-ray energy measurement H and a lower x-ray energy measurement L from each detector element position, and carries out initial processing known in the art to derive, from the raw x-ray data, a set of pixel values for a projection image. Each pixel value comprises a high energy value H and a low energy value L. This can be achieved by rapidly alternating the energy level of the x-rays from source 20 between a higher and a lower range of x-ray energies, for example by rapidly rotating or otherwise moving a suitable filter in or out of the x-rays before they reach patient 26, or by controlling the x-ray tube output, and/or by using an x-ray detector 28 that can discriminate between energy ranges to produce H and L measurements for each pixel position, e.g. by having a low energy and a high energy detector element side-by-side or on top of each other for respective positions in the detector array. The H and L x-ray measurements for the respective pixel positions are computer-processed as known in the art to derive estimates of various parameters, including, if desired, body composition (total mass, fat mass, and lean mass).

Figure 2A:
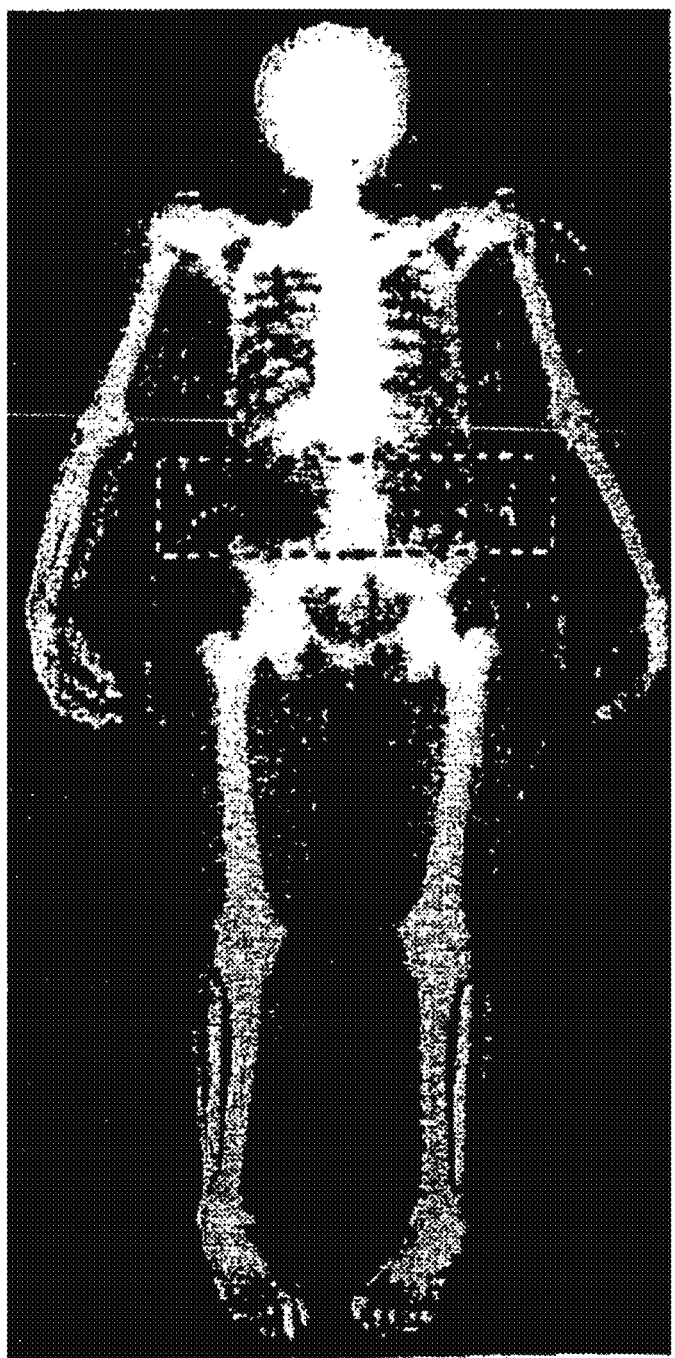
FIG. 2a illustrates a PA projection image of a patient taken with a DXA system.
Figure 2B:
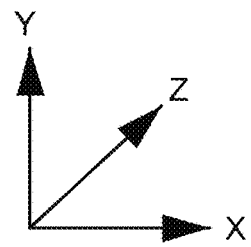
Figure 2B:

A PA projection image taken with the DXA system is illustrated in FIG. 2a. FIG. 2b is an enlarged view of the projection image of the relatively thick slice of the body indicated by the broken line rectangle in FIG. 2a. As suggested by FIGS. 2a and 2b, pixel values are derived from x-ray measurements for a body slice that is along the z-x plane and has a thickness (w) in the y-direction. For example, several hundred pixel values in the x-direction and a several pixel values in the y-direction are derived from the raw x-ray data. Typically but not necessarily, the body slice thickness w along the y-direction is several mm, e.g. 10-15 mm.

Figure 3:
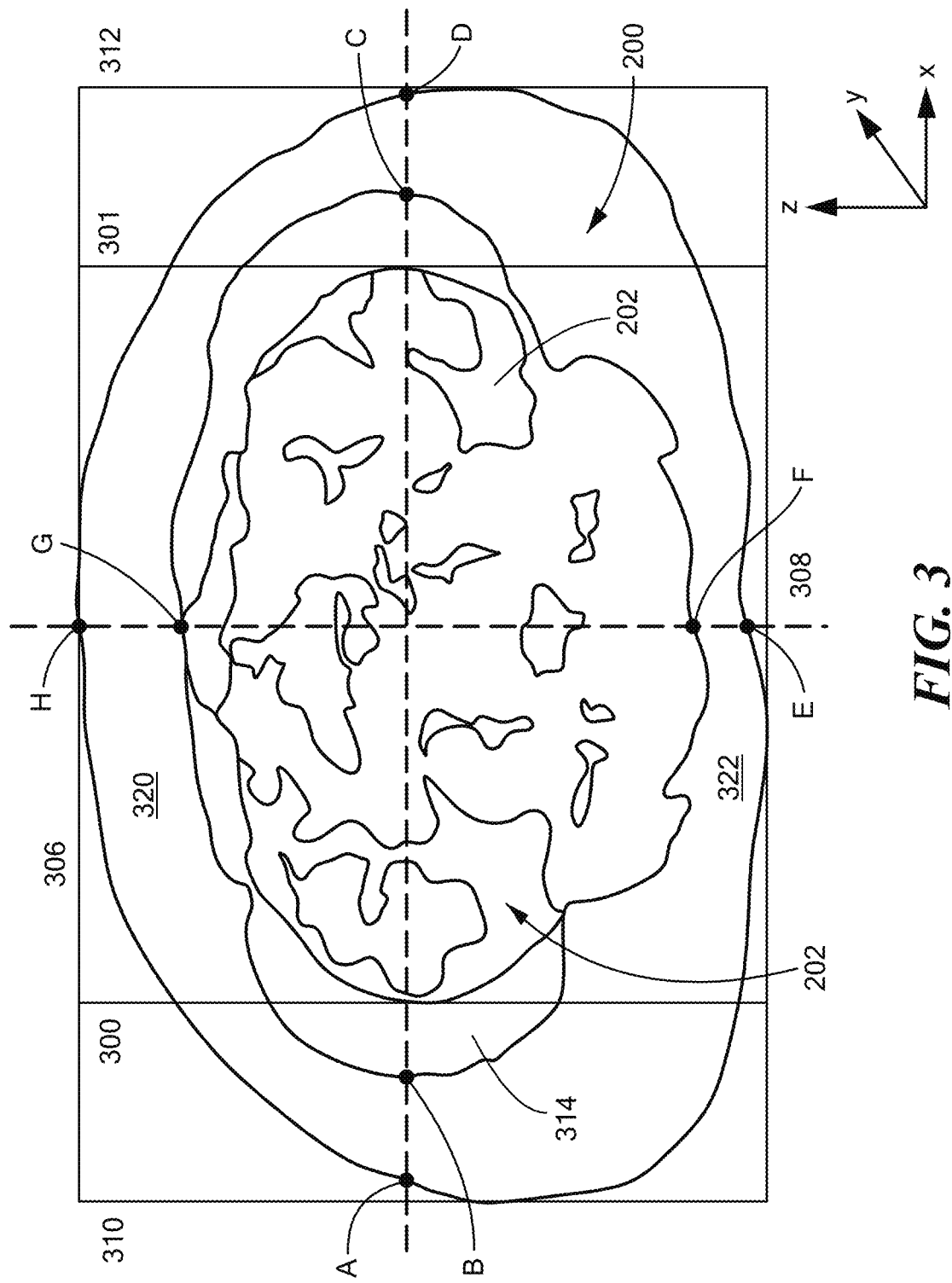
FIG. 3 illustrates a cross-sectional image of a body slice.

FIG. 3 illustrates an x-ray image of a section or slice parallel to a z-x plane through the abdominal region of an obese patient taken with a CT system. The image shows a ring 200 (non-circular) of subcutaneous adipose tissue (SAT) and regions 202 of visceral adipose tissue (VAT).

Figure 4:
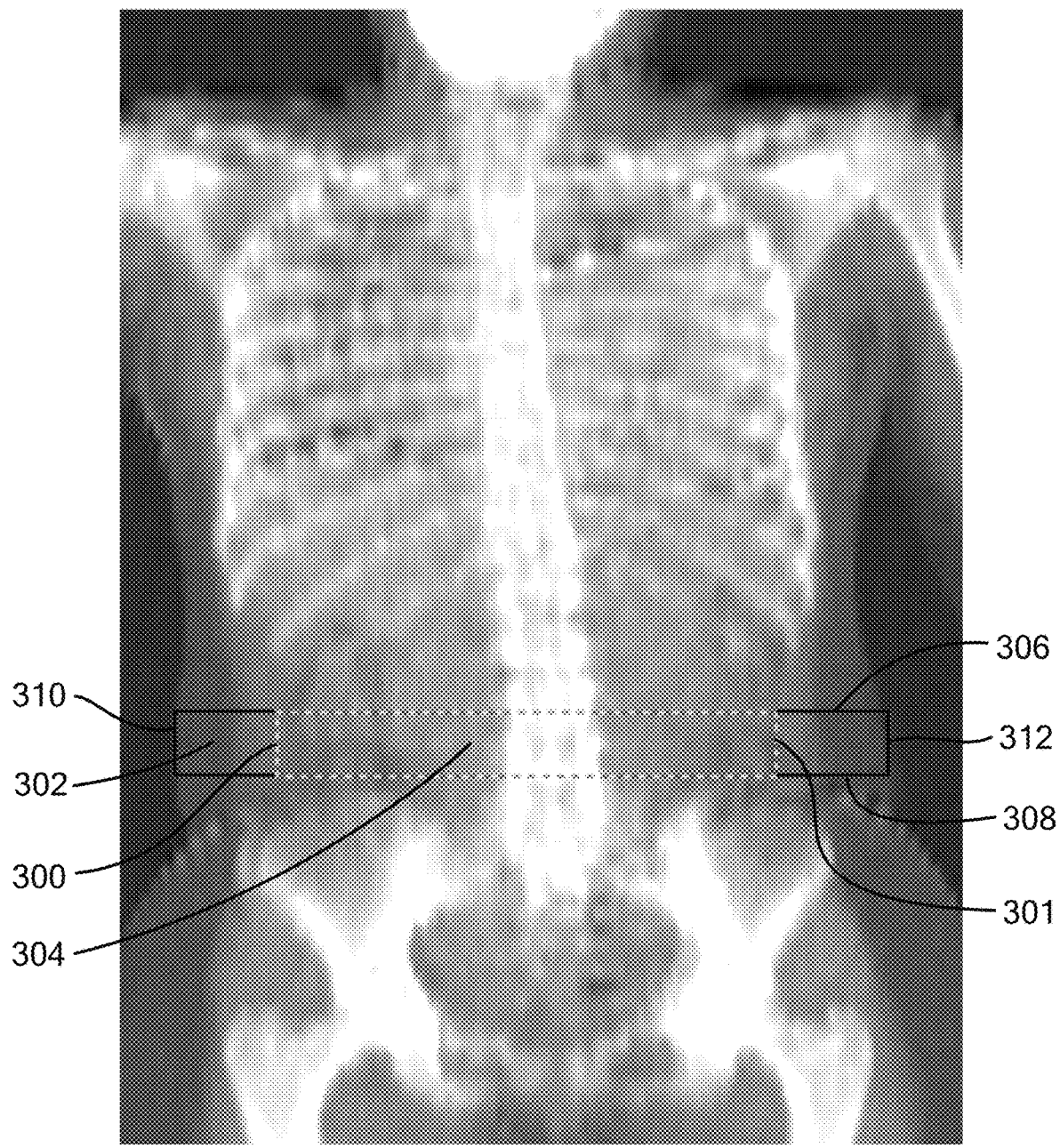
FIG. 4 illustrates placement of a large "abdominal" region and a smaller "abdominal cavity" region.

Referring to FIG. 3 and FIG. 4, in accordance with one embodiment of the invention % VAT is estimated with a DXA system using an empirical technique. A region of interest (ROI) is placed on a DXA scan to delineate various anatomical regions, e.g. arms, trunk, legs, etc. in accordance with the instructions in the User's Guide for the Hologic DXA scanner. After the ROI has been placed on the scan, a large "abdominal" region 302 and a smaller "abdominal cavity" region 304, both rectangular in shape and 4 scan lines (5 cm) high, are placed on the subject's abdomen 1-2 scan lines (1.5-2.5 cm) above the top of the pelvis region at the level of vertebral body L4. The large "abdominal" region 302 is defined by boundaries 306, 308, 310, 312, and extends completely across the abdomen from one side to the other. The smaller "abdominal cavity" region 304 is defined by boundaries 300, 301, 306, 308, centered within the large region, and extends across the inner abdominal cavity. The large "abdominal" region can be placed by the user based on visual inspection of the image. However, in accordance with an embodiment of the invention the "abdominal" region is automatically placed by a software tool that is stored in non-transitory computer readable memory and run by processing hardware. For example, the software tool may place the "abdominal" region using various anatomical landmarks and the position of the upper ROI line delineating the pelvis for reference.

Figure 5:
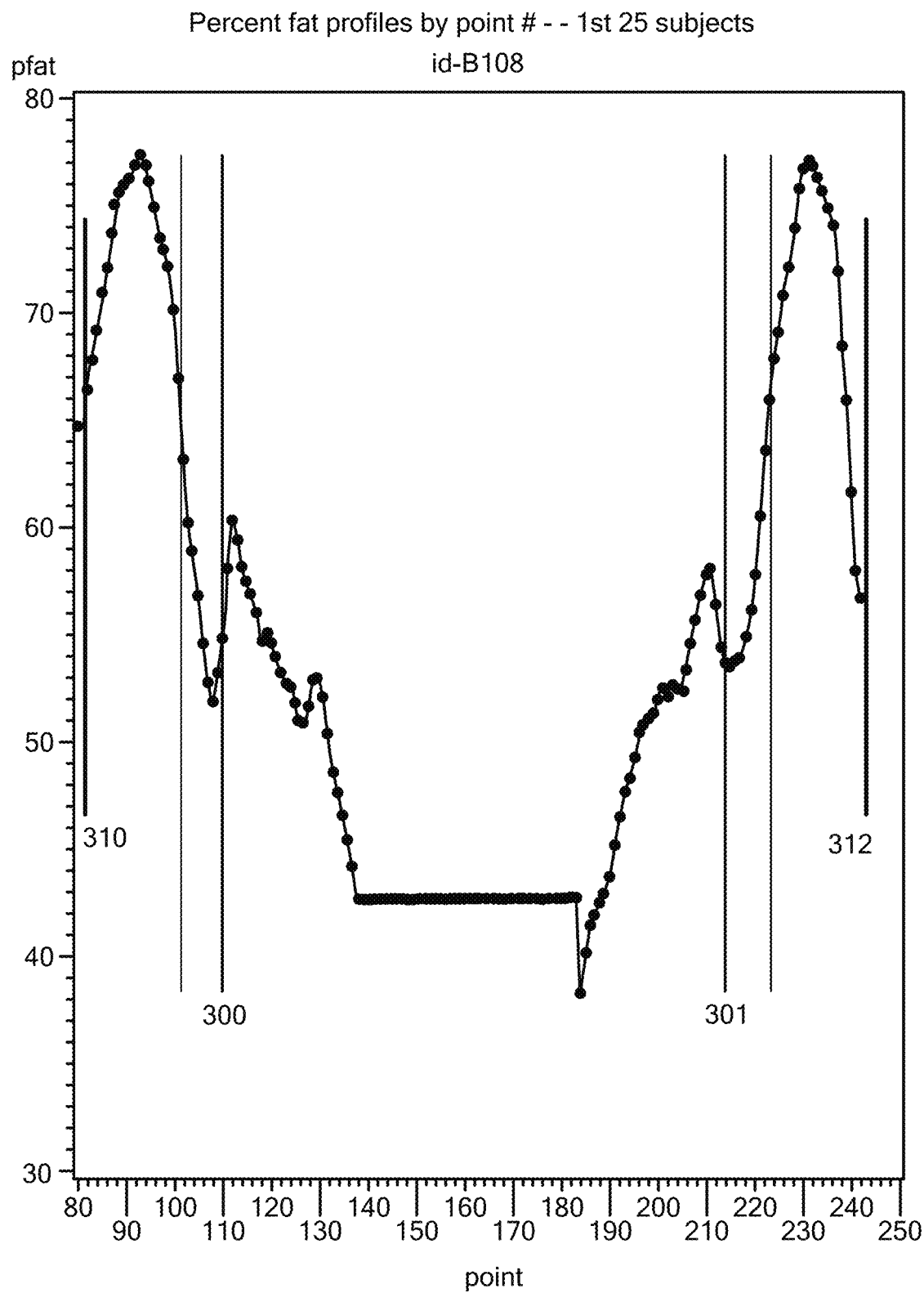
FIG. 5 illustrates a % fat profile and inflection points used for placement of the abdominal cavity region.

Referring to FIGS. 3 through 5, the software tool may also automatically place the smaller "abdominal cavity" region 304 within the larger region 302. In one embodiment this is accomplished with an algorithm which places boundaries based on % Fat inflection. The upper and lower boundaries 306, 308 of the "abdominal cavity" region are superimposed over the larger region such that the upper and lower coordinates of both regions are identical. The left and right boundaries 300, 301 of the "abdominal cavity" region are then placed by the algorithm. In particular, the algorithm initially operates on percent fat profile data corresponding to a position inside the left and right boundaries 310, 312 of the large abdominal region, e.g., at the point where the subcutaneous fat layer ends, and proceeds by operating on data corresponding to an adjacent set of pixels moving in toward the center the body from the left and right sides. Initially, % Fat decreases steadily as the x-ray beam enters the abdominal muscle band 314. Typically after one or two cm (10-20 pixels) the trend of decreasing % Fat reverses as the DXA beam exits the abdominal muscle wall and enters the inner visceral cavity. At this point the % Fat values start to increase. This inflection point, which is indicative of the innermost extent of the abdominal muscle wall, is detected by the algorithm, e.g., by identifying that the % Fat values of two consecutive pixels are higher than the preceding pixel. The "abdominal cavity" region boundaries 300, 301 are set at the inflection point.

In practice the abdominal cavity can be located easily on one side of the body but may be difficult to find on the other. In this case the size and location of the cavity wall that was found can be mirrored to the other side by taking advantage of the presence of bilateral symmetry in the DXA anterior-posterior projection of the human body.

A linear regression technique that accounts for SAT between the boundaries of the "abdominal cavity" region is used to estimate VAT. The large "abdominal" region defined by boundaries 306, 308, 310, 312 provides a measurement of total adipose tissue in a 5 cm wide region across the entire width of the subject just above the pelvis at the level of the $4^{th}$ lumbar vertebrae. The smaller "abdominal cavity" region defined by boundaries 300, 301, 306, 308 provides a measurement of the adipose tissue in the same 5 cm wide region of the abdominal cavity plus whatever subcutaneous fat is present above (at region 320) and below (at region 322) the cavity region in the two dimensional DXA projection. Constant percent fat values at the center of the plot in FIG. 5 indicate image pixels where bone is present and percent fat cannot be directly measured. However, techniques for estimating percent fat values for the region where bone is present and percent fat cannot be directly measured are known. The measurement (Abd. Adipose Mass) of total adipose tissue in a 5 cm wide region across the entire width of the subject just above the pelvis at the level of the $4^{th}$ lumbar vertebrae and the measurement (Cavity Adipose Mass) of the adipose tissue in the same 5 cm wide region of the abdominal cavity plus whatever subcutaneous fat is present above and below the cavity region in the two dimensional DXA projection is combined in a linear equation that is highly correlated with VAT measured by quantitative computed tomography in order to estimate VAT as:

$$\text{DXA VAT} = J \cdot \text{Cavity Adipose Mass} - K \cdot (\text{Abd. Adipose Mass} - \text{Cavity Adipose Mass}) + b, \qquad \text{Eq. 1}$$

where J and K are constants that optimize the correlation between DXA VAT and VAT measured by computed tomography, and b is the intercept term of the linear equation. It should be noted that the values of J, K and b are not necessarily that same for all subjects. For example, values of J, K and b can be dependent upon age, gender, ethnicity, weight, height, body mass index, waist circumference, and other anthropomorphic variables. Those skilled in the art will understand how to determine those constants in view of this disclosure.

The results of the processes described above can be in various forms and can be used for a variety of purposes. For example, displays of numerical values can be used in assessing the health, treatment options, or treatments of a patient by a health professional. As another example, such numerical values or estimates derived therefrom can be used as inputs to automated systems for similar assessment or for treatment planning. As yet another example, parameters related to fat metrics can be displayed and recorded or printed as a part of an otherwise typical report including x-ray images and other DXA-produced information for a patient.

Estimates of visceral fat derived as discussed above can be shown in a variety of ways. They can be displayed alone, or in combination with known or expected ranges of comparable estimates for populations believed to be "normal" or "healthy," which ranges can be matched to the estimates for a patient by some characteristic such as age, sex, and/or ethnicity. The normal or healthy ranges for such characteristics can be obtained by retrospective analysis of already completed studies and/or from new studies to obtain the data. A VAT metric for a patient can be compared with a VAT metric for the same patient taken at a different time to estimate the change and/or the rate of change, for example to see if visceral fat parameters have improved or have deteriorated over some period of time or in relation to some treatment or regimen. Such changes also can be matched to expected or known or estimated ranges to see if the change or rate of change for a patient is statistically significant as distinguished from a change within the precision range of the estimate. The VAT estimates derived as discussed above, or metrics based on such estimates, can be used in other ways as well. One non-limiting example is to produce reports similar to those produced for BMD (bone mineral density) in current commercial bone densitometry (DXA) systems but for metrics of visceral fat (VAT) rather than BMD estimates.

Figure 6:
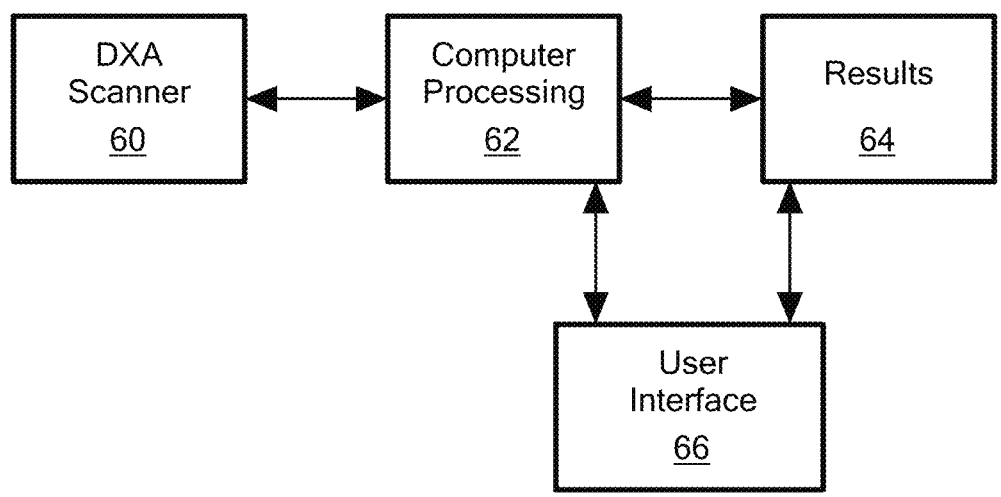
FIG. 6 is a block diagram of a DXA system useful for estimating visceral adipose tissue.

FIG. 6 illustrates in block diagram form a DXA system carrying out the processes described above for estimating VAT. The system can be one of the current DXA systems offered commercially by the assignee programmed to carry out the disclosed processes, using programming that a person of ordinary skill in the art can apply to a particular commercially available DXA system without undue experimentation, given the teachings in this patent specification. The system includes a scanner 60, computer processing unit 62, user interface 66, and a results presentation unit 64. The scanner may include an x-ray source and x-ray detector. Scanner 60 also includes appropriate other components known in the art, such as power and control units, and operates to generate dual energy or single energy x-ray measurements of the selected region or slice of a patient's body. The computer processing unit 62 includes processing hardware and non-transitory computer readable memory for controlling scanner 60 and processing x-ray measurements obtained thereby in accordance with the techniques described above under corresponding programming. A results presentation unit 64 displays, prints, stores, and/or sends for further processing or storage, results such as in the form of images and/or curves and/or numeric results indicative of VAT or % VAT, or some other parameter related to visceral fat or other parameter discussed above, including in the immediately preceding paragraph. Units 62 and 64 communicate interactively with a user input unit 66. The actual physical arrangement of system components may differ from the functional illustration in FIG. 6.

The disclosure above is mainly in terms of SAT and VAT of human patients, but it should be clear that its approach is applicable in other fields as well, such as in analysis of other subjects, such as live animals and carcasses. Finally, while a currently preferred embodiment has been described in detail above, it should be clear that a variation that may be currently known or later developed or later made possible by advances in technology also is within the scope of the appended claims and is contemplated by and within the spirit of the detailed disclosure.

Figure 7:
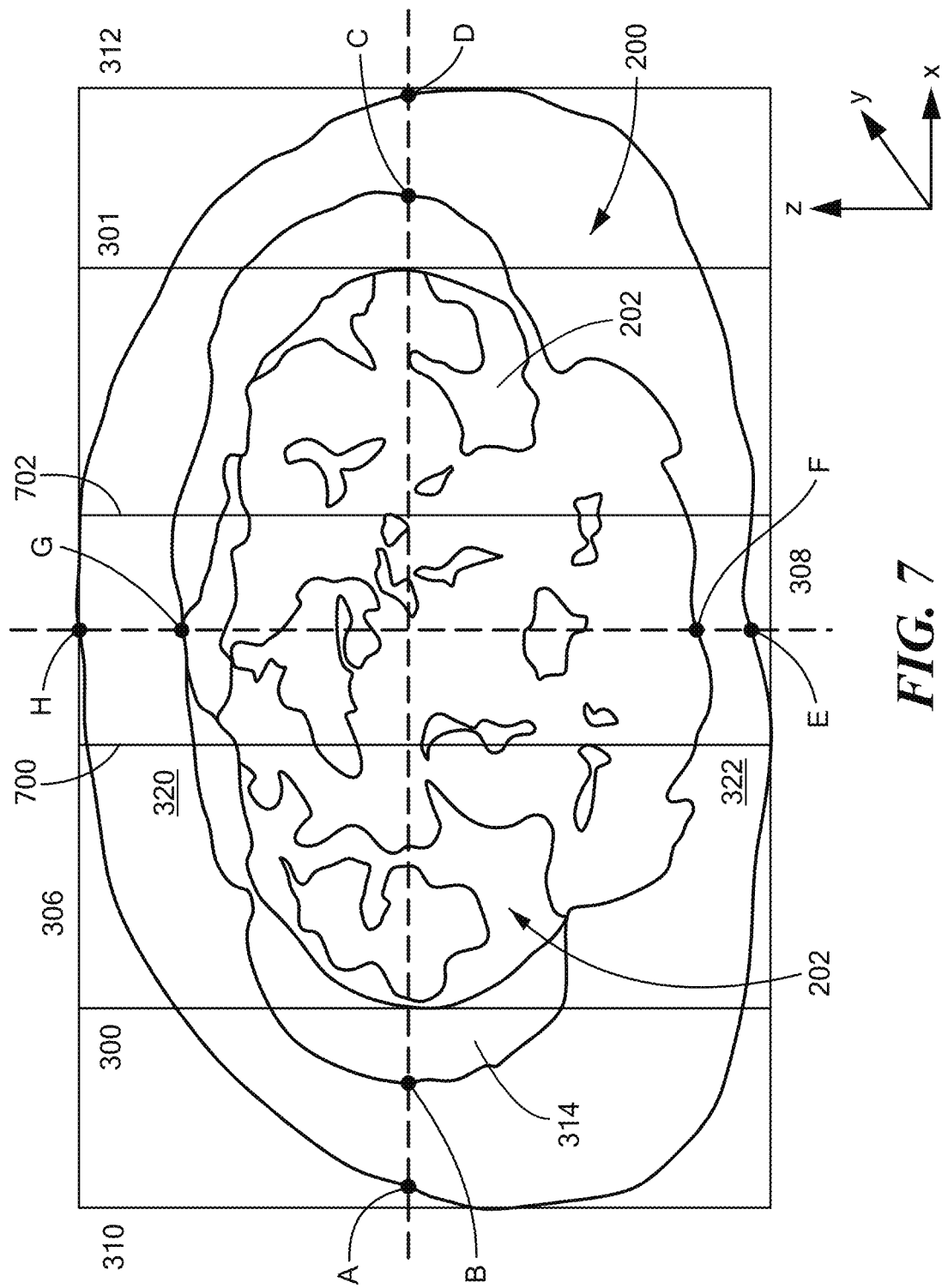
FIG. 7 is a cross-sectional image of a body slice which illustrates use of more than two regions.

FIG. 7 is a cross-sectional image of a body slice which illustrates an alternative embodiment utilizing more than two regions. The large "abdominal" region defined by boundaries 306, 308, 310, 312 provides a measurement of total adipose tissue in a 5 cm wide region across the entire width of the subject just above the pelvis at the level of the $4^{th}$ lumbar vertebrae. A smaller "cavity" region which includes a first portion defined by boundaries 300, 700, 306, 308 and a second portion defined by boundaries 702, 301, 306, 308 provides a measurement of the adipose tissue in the same 5 cm wide region of the abdominal cavity, exclusive of the spinal region, and plus whatever subcutaneous fat is present above (at region 320) and below (at region 322) the cavity region in the two dimensional DXA projection. The "spinal" region defined by boundaries 700, 306, 702, 308 provides a measurement of adipose tissue where bone is present and percent fat cannot be directly measured. A generalized linear equation for combining the measurements of adipose tissue in order to estimate VAT with three regions can be represented as:

$$\text{DXA VAT} = J^*\text{Region1} + K^*\text{Region2} + L^*\text{Region3} + b, \quad \text{Eq. 2}$$

where J, K and L are constants that optimize the correlation between DXA VAT and VAT measured by computed tomography, and b is the intercept term of the linear equation. As in the previously described embodiment, the values of the constants (here J, K, and L) and intercept b are not necessarily that same for all subjects. For example, values of J, K, L and b can be dependent upon age, gender, ethnicity, weight, height, body mass index, waist circumference, and other anthropomorphic variables. Those skilled in the art will understand how to determine those constants in view of this disclosure. Furthermore, the two region and three region embodiments are merely exemplary, and any number of regions could be defined and utilized to estimate VAT.

In an alternative embodiment polynomial expansion is used to estimate VAT. A generalized equation for combining the measurements of adipose tissue using polynomial expansion in order to estimate VAT can be represented as:

$$\text{DXA VAT} = J1(\text{Region1}) + J2(\text{Region1})^2 + J3(\text{Region1})^2 + \ldots \quad \text{Eq. 3}$$

where Jn and constants associated with the polynomial expansion of the other regions (eg. $K_n$ and $L_n$) optimize the correlation between DXA VAT and VAT measured by computed tomography. As in the previously described embodiment, the values of the constants are not necessarily that same for all subjects, and can be dependent upon age, gender, ethnicity, weight, height, body mass index, waist circumference, and other anthropomorphic variables.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A method comprising:
    acquiring x-ray measurements using a dual-energy x-ray absorptiometry (DXA) system for respective pixel positions related to a two-dimensional projection image of a portion of a subject's abdomen, wherein the x-ray measurements are dual-energy x-ray measurements;
    placing a plurality of regions of the image, wherein said placing includes placing a first region of the image which extends from a first side of the abdomen to a second side of the abdomen, and placing a second region on or within the first region, wherein each of the plurality of regions of the image is a two-dimensional region, and wherein the second region is automatically placed based on fat mass values obtained from DXA measurements;
    computer processing to combine the plurality of regions to provide an estimate of visceral fat (VAT) in which said estimate of visceral fat is distinguishable from subcutaneous fat (SAT); and
    displaying at least one of said estimate of visceral fat and a metric based on said estimate of visceral fat.

2. The method of claim 1 wherein the placing of the second region is based on an inflection of % total fat values obtained from DXA measurements of two consecutive pixel positions.

3. The method of claim 2 wherein the placing of the second region is based on computer processing the first region.

4. The method of claim 1 wherein the second region has a first side and a second side, wherein the first side of the second region is spaced inwardly from the first side of the abdomen, and wherein the second side of the second region is spaced inwardly from the second side of the abdomen.

5. The method of claim 1 wherein the plurality of regions is combined using polynomial expansion.

6. The method of claim 1 wherein the second region extends across an inner abdominal cavity from the first side to the second side between innermost extents of an abdominal muscle wall.

7. The method of claim 1 wherein the placing further comprises placing a third region of the image, wherein the third region is on or within the first region and is placed where bone is present and percent fat cannot be directly measured, and wherein the second region extends across an inner abdominal cavity from the first side to the second side between innermost extents of an abdominal muscle wall but is exclusive of the third region.

8. The method of claim 1 wherein the placing of at least two regions of the plurality of regions of the image comprises computer processing at least some of the x-ray measurements.

9. The method of claim 1 wherein the placing of the first region of the image comprises using an anatomical landmark and a preselected region of interest line.

10. The method of claim 1 wherein the second region extends across an inner abdominal cavity from the first side to the second side between innermost extents of an abdominal muscle wall and wherein the second region is placed by identifying a left and a right innermost extent of abdominal muscle wall by identifying inflection of adipose tissue values.

11. A method comprising:
    acquiring x-ray measurements for respective pixel positions related to a two-dimensional projection image of a portion of a subject's abdomen, wherein the x-ray measurements are dual-energy x-ray measurements;
    placing a plurality of regions of the image, wherein each of the plurality of regions of the image is a two-dimensional region and wherein at least one of the plurality of regions is automatically placed based on fat mass values obtained from DXA measurements;
    computer processing to combine the plurality of regions to provide an estimate of visceral fat, wherein combining the plurality of regions uses polynomial expansion; and
    displaying at least one of said estimate of visceral fat and a metric based on said estimate of visceral fat.

12. A method comprising:
    acquiring x-ray measurements for respective pixel positions related to a two-dimensional projection image of a portion of a subject's abdomen, wherein the x-ray measurements are dual-energy x-ray measurements;
    placing a plurality of regions of the image, wherein the placing includes placing a first region of the image which extends from a first side of the abdomen to a second side of the abdomen and placing a second region which extends across an inner abdominal cavity from the first side to the second side between innermost extents of an abdominal muscle wall, and wherein said placing of said second region includes identifying a left and a right innermost extent of abdominal muscle wall by identifying inflection of adipose tissue values obtained from DXA measurements, wherein each of the plurality of regions of the image is a two-dimensional region;
    computer processing to combine the plurality of regions to provide an estimate of visceral fat, wherein the computer processing includes computer processing at least some of the x-ray measurements for placing the second region of the image; and
    displaying at least one of said estimate of visceral fat and a metric based on said estimate of visceral fat.

* * * * *